US012232945B2

(12) United States Patent
Hashmi et al.

(10) Patent No.: US 12,232,945 B2
(45) Date of Patent: Feb. 25, 2025

(54) PRELOADED DMEK HOLDER

(71) Applicant: University of Iowa Research Foundation, Iowa City, IA (US)

(72) Inventors: Syed M. A. Muqsit Hashmi, Coralville, IA (US); Leela Raghava Jaidev Chakka, Iowa City, IA (US); Aliasger K. Salem, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 856 days.

(21) Appl. No.: 17/360,808

(22) Filed: Jun. 28, 2021

(65) Prior Publication Data

US 2021/0401562 A1 Dec. 30, 2021

Related U.S. Application Data

(60) Provisional application No. 63/045,395, filed on Jun. 29, 2020.

(51) Int. Cl.
*A61F 2/00* (2006.01)
*A01N 1/02* (2006.01)
*A61F 2/14* (2006.01)

(52) U.S. Cl.
CPC .......... *A61F 2/0095* (2013.01); *A01N 1/0273* (2013.01); *A61F 2/142* (2013.01); *A61F 2230/0065* (2013.01); *A61F 2230/0067* (2013.01); *A61F 2230/0069* (2013.01)

(58) Field of Classification Search
CPC ............. A61F 2/0095; A61F 2/142; A61F 2230/0065; A61F 2230/0067; A61F 2230/0069; A01N 1/0273
USPC ...................................................... 435/284.1
See application file for complete search history.

(56) References Cited

U.S. PATENT DOCUMENTS 10,481,051 B2 * 11/2019 Tran .................. C12N 5/0693
2020/0337826 A1 * 10/2020 Perry .................. A61L 29/04

* cited by examiner

*Primary Examiner* — William H. Beisner
(74) *Attorney, Agent, or Firm* — Goodhue, Coleman & Owens, P.C.

(57) ABSTRACT

A Descemet Membrane Endothelial Keratoplasty (DMEK) holder for placement within a vial for supporting a corneal tissue inserter is provided. The DMEK holder includes a top and an opposite bottom, at least one support member extending between the top and the bottom, with a bottom portion of the at least one support member sized and shaped to fit against a bottom inner surface of the vial to thereby support the corneal tissue inserter within the vial, and a first annular member having an opening sized and shaped such that a bottom end of the corneal tissue inserter is insertable through the opening and the first annular member separates the corneal tissue inserter from an inner surface of the vial and positions the corneal tissue inserter within the vial away from inner surfaces of the vial to thereby improve retrieval of the corneal tissue inserter by a surgeon.

20 Claims, 8 Drawing Sheets

PRELOADED DMEK HOLDER

RELATED APPLICATION

This application claims priority to U.S. Provisional Patent Application No. 63/045,395, filed Jun. 29, 2020, hereby incorporated by reference in its entirety.

FIELD OF THE INVENTION

The present invention relates to Descemet Membrane Endothelial Keratoplasty (DMEK). More particularly, but not exclusively, the present invention relates to preloaded DMEK holders.

BACKGROUND

DMEK is a technique where the Descemet Membrane (DM) and endothelium are harvested from a donor and transplanted to a recipient. This technique is potentially advantageous over other types of keratoplasty techniques including quicker visual rehabilitation, better optical quality, and less costly surgical equipment requirements.

However, despite its advantages, problems with implementation of DMEK still remain. One of these problems relates to the need to handle the DM/endothelial complex in a manner to avoid or at least minimize damage to the DM/endothelial cells. The DM sheet may be very thin (e.g. 10 microns) and may roll up in the manner of a scroll and thus may be referred to as a DMEK scroll. The DMEK scrolls may be preserved in media preloaded into injectors or cornea transplant inserters which are placed in vials during transport and shipping from a processing eye bank to the operating room. Yet despite these efforts to minimize damage, damage may still occur during transport and shipping. What is needed is improved handling.

Therefore, what is needed is methods, systems, and apparatus for reducing damage of DMEK scrolls during transport and shipping such as from a processing eye bank to an operating room.

SUMMARY

Therefore, it is a primary object, feature, or advantage of the present invention to improve over the state of the art.

It is a further object, feature, or advantage of the present invention to support a cornea transplant inserter during transport and/or shipping from a processing eye bank to an operating room.

It is a still further object, feature, or advantage of the present invention to reduce damage to cornea tissue during transport or shipping.

Another object, feature, or advantage is to support a cornea transplant inserter in a manner that facilitates easy retrieval of the corneal transplant inserter from a vial by a surgeon.

Yet another object, feature, or advantage is to provide for vertical transportation and shipment of preloaded DMEK tissue as opposed to a horizontal method.

A further object, feature, or advantage is to protect the corneal tissue inserter, such as a Modified Jones Tube-DMEK EB within the preservation media vial during the shipping process.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

According to one aspect, a Descemet Membrane Endothelial Keratoplasty (DMEK) holder for placement within a vial for supporting a corneal tissue inserter is provided. The DMEK holder includes a top and an opposite bottom, at least one support member extending between the top and the bottom, with a bottom portion of the at least one support member sized and shaped to fit against a bottom inner surface of the vial to thereby support the corneal tissue inserter within the vial, and a first annular member having an opening sized and shaped such that a bottom end of the corneal tissue inserter is insertable through the opening and the first annular member separates the corneal tissue inserter from an inner surface of the vial and positions the corneal tissue inserter within the vial away from inner surfaces of the vial to thereby promote improved access to the corneal tissue inserter when a top of the vial is open. The at least one support member may include a first elongated support member, a second elongated support member, and a third elongated support member each of which may be cylindrically shaped or otherwise shaped. Each of the first elongated support member, the second elongated support member, and the third elongated support member may be spaced apart around an outer edge of the first annular member. The DMEK holder may further include a second annular member, the second annular member positioned along the at least one support member below the first annular member, the second annular member having an opening sized and shaped such that the bottom end of the corneal tissue inserter is insertable through the opening. The DMEK holder may further include an end support extending downwardly from a bottom surface of the second annular member and sized and shaped to support an end of the corneal tissue inserter. The end support may be generally conical in shape or otherwise shaped.

According to another aspect, a system includes a vial having a bottom end and an opposite top end, the top end having an opening for accessing contents of the vial, a corneal tissue inserter, and a holder disposed within the vial, wherein the holder is configured to support the corneal in a vertically upright position. The holder includes a top and a bottom with at least one support member extending between the top and the bottom, and a first annular member at the top of the at least one support member, the first annular member having an opening therein sized and shaped such that the bottom end of the corneal tissue inserter is insertable through the opening. The corneal tissue inserter may preloaded with corneal tissue.

BRIEF DESCRIPTION OF THE DRAWINGS

Illustrated embodiments of the disclosure are described in detail below with reference to the attached drawing figures, which are incorporated by reference herein.

DETAILED DESCRIPTION

A preloaded DMEK holder may be used to support a cornea transplant inserter during transport and shipping from a processing eye bank or other facility to an operating room. The holder prevents damage to the cornea tissue and benefits the surgeon for easier access to the inserter in preparation for cornea transplant surgery.

Figure 1:
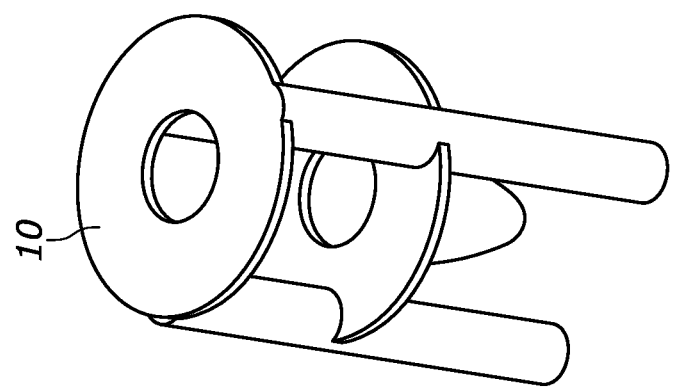
FIG. 1 illustrates one example of a cornea tissue inserter next to a DMEK holder.
Figure 1:
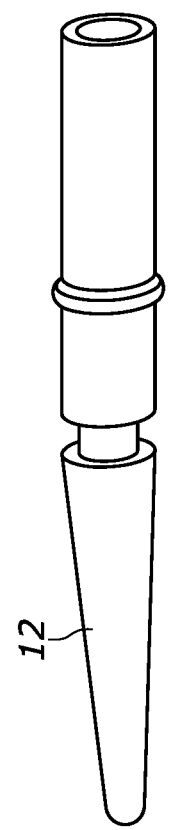

FIG. 1 illustrates an example of a DMEK holder 10 adjacent to an example of a corneal tissue inserter. The corneal tissue inserter shown is a modified Jones tube-DMEK EB.

Figure 2:
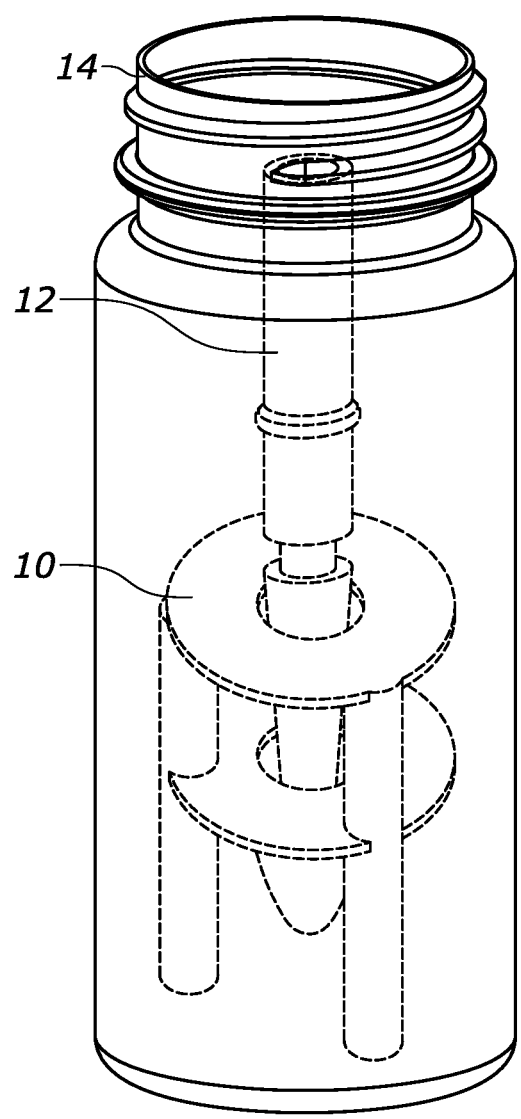
FIG. 2 illustrates a vial in which the DMEK holder is providing support for the cornea tissue inserter.

FIG. 2 illustrates a preservation media vial 14 having a top opening through which the corneal tissue inserter 12 and the DMEK holder 10 may be placed. Note that as shown, the DMEK holder 10 provides multiple benefits. First, the corneal tissue inserter is protected such as during shipping. The DMEK holder 10 prevents the corneal tissue inserter from contacting the inner walls of the vial 14 thereby providing additional protection for the corneal tissue inserter. Second, the DMEK holder 10 positions the corneal tissue inserter such that it is easy for the surgeon to retrieve as the corneal tissue inserter is maintained in a generally upright vertical position within the vial.

Figure 3:
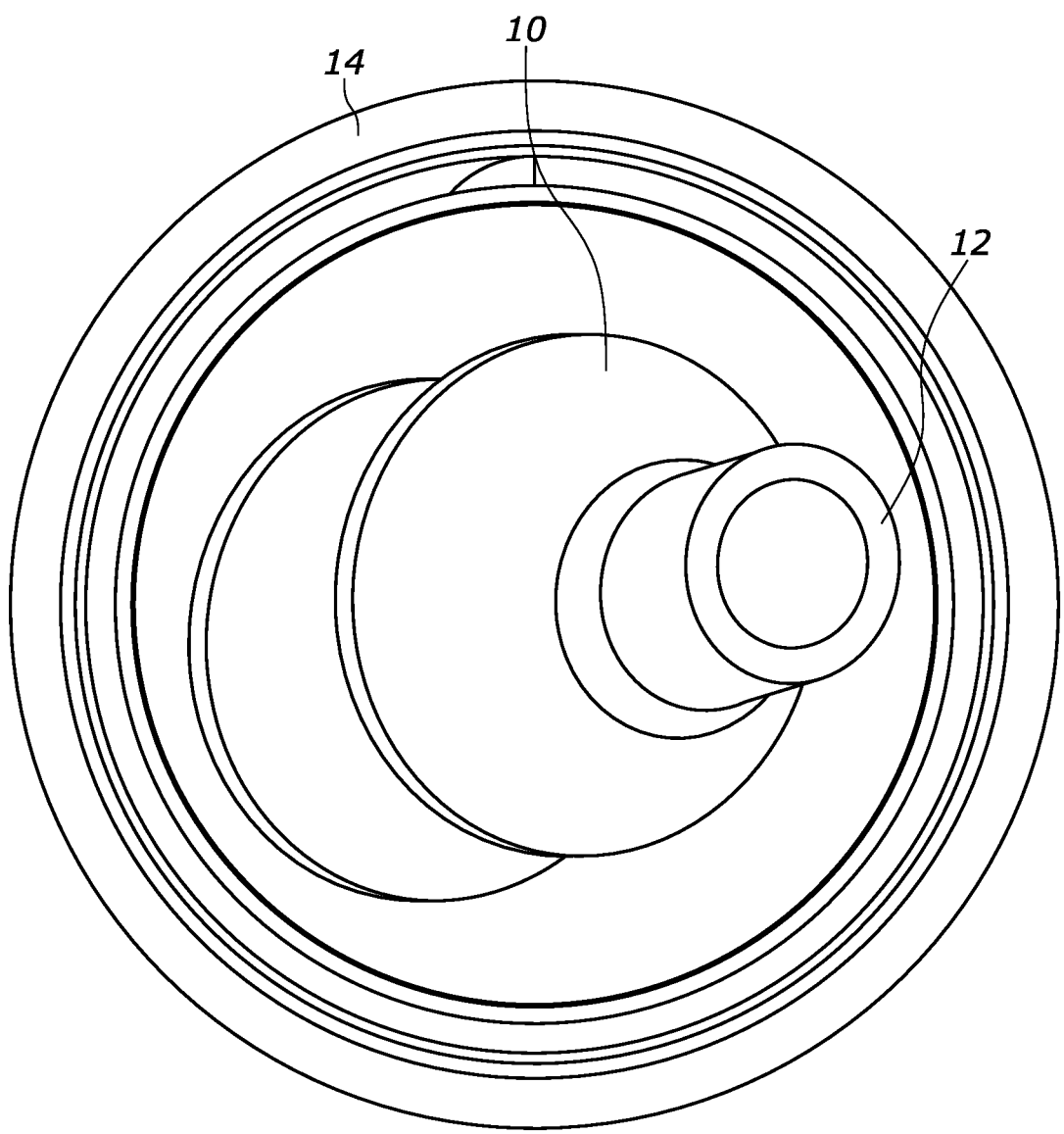
FIG. 3 is a top view of the vial in which the DMEK holder is providing support for the cornea tissue inserter.

FIG. 3 is a top view of the vial 14 such as might be viewed by a surgeon. Note that the corneal tissue inserter 12 is readily accessible at the top of the vial but is not resting against a surface of the vial. The DMEK holder 10 is supporting the corneal tissue inserter so as to prevent contact between the corneal tissue inserter and the vial.

Figure 4:
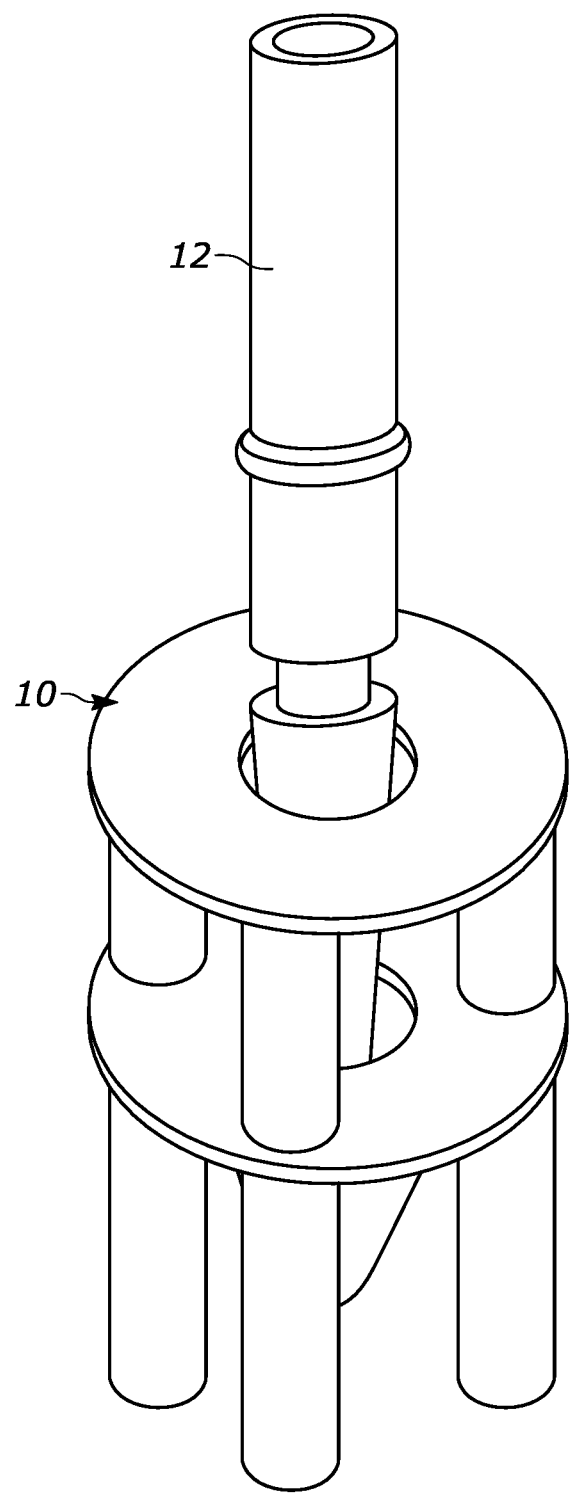
FIG. 4 illustrates the cornea tissue inserter when inserted into the DMEK holder with the DMEK holder supporting the cornea tissue inserter in a generally upright or vertical position.

FIG. 4 shows a view of the corneal tissue inserter 12 positioned in the DMEK holder 10. The DMEK holder supports the corneal tissue inserter 12 in a generally vertical upright position as shown.

Figure 5:
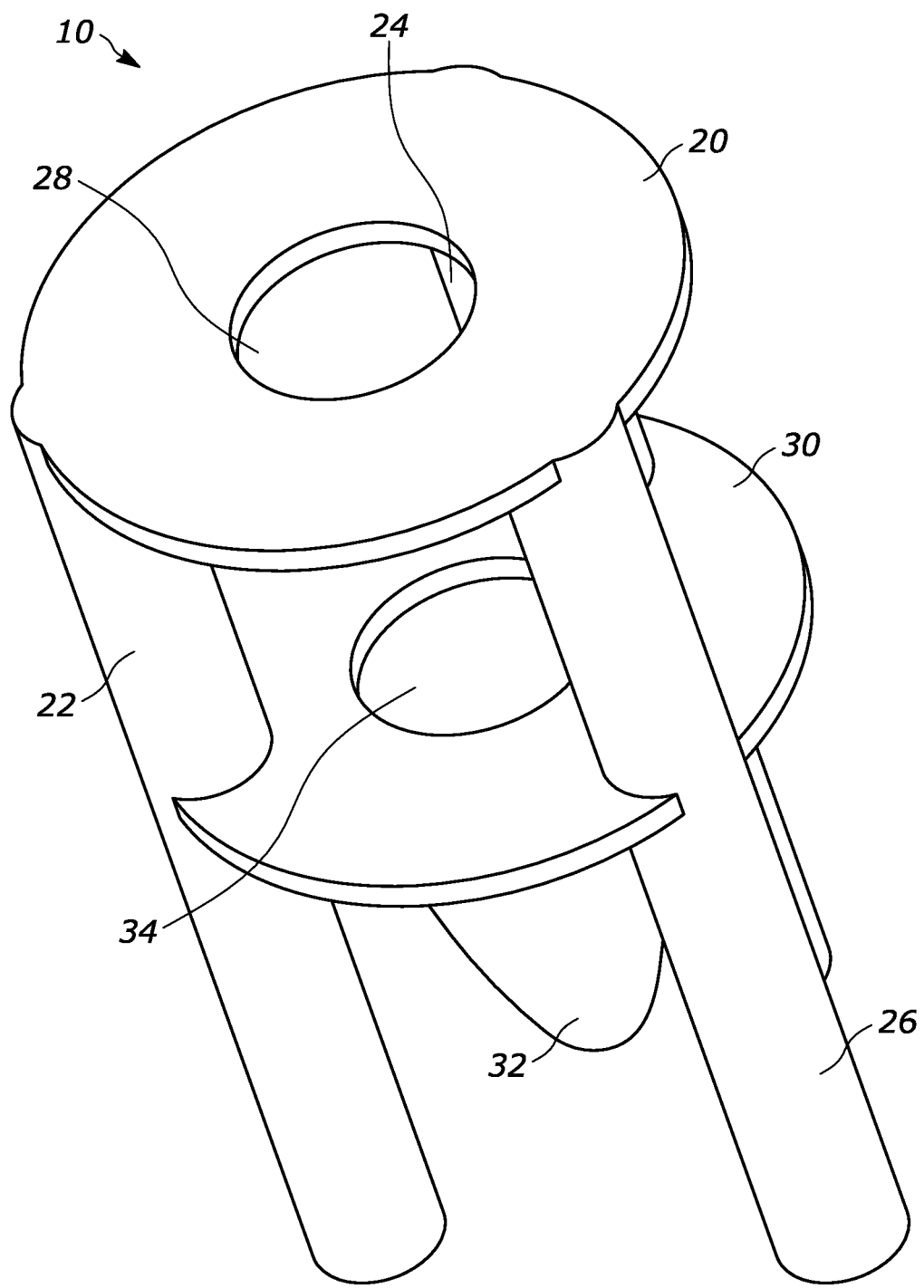
FIG. 5 is a perspective view of one example of the DMEK holder.

FIG. 5 illustrates one example of the DMEK holder 10 in more detail. The DMEK holder 10 has a top and an opposite bottom. Three support members 22, 24, 26 are shown in the form of cylindrical support members, each of which extends between the top and bottom of the DMEK holder. Although three support members 22, 24, 26 are shown which may be spaced evenly around a circle, other numbers of support members are contemplated and other structural configurations for the support member are contemplated. At the top is a first annular member 20 which is circular as shown. The first annular member 20 has an opening 28 sized and shaped such that a bottom end of the corneal tissue inserter is insertable through the opening 28. A second annular member 30 is shown which is positioned below the first annular member 20. There is an opening 34 in the second annular member 30. An end support 32 may extend downwardly from the second annular member 30. The end support 32 may support an end of the corneal tissue inserter. The end support may be in the form of an end cone or may be otherwise shaped to support the end of the corneal tissue inserter. The DMEK holder 10 may be integrally formed from a single material such as plastic.

Figure 6:
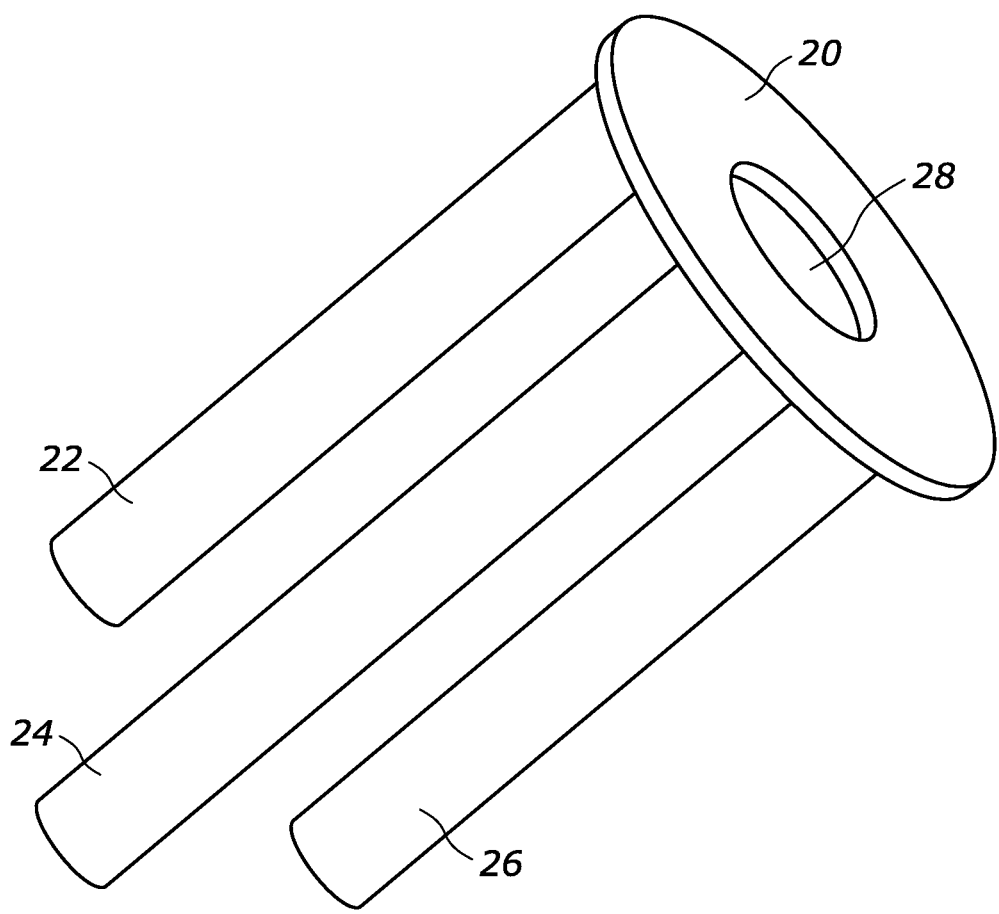
FIG. 6 is a perspective view of another example of the DMEK holder.

FIG. 6 is a perspective view of a DMEK holder or portions of a DMEK holder. As shown in FIG. 6, the DMEK holder has a first annular member 20 with an opening 28 sized and shaped to such that the bottom end of the corneal tissue inserter may pass therethrough and in an operative position, the sides of the corneal tissue inserter may rest against or proximate to the first annular member 20. Three support members 22, 24, 26 extend downwardly from the first annular member 20 and in the operative position may come to rest against a bottom inner surface of the vial. The three support members 22, 24, 26 may be cylindrical in shape or otherwise shaped. The three support members 22, 24, 26 may be substantially equally spaced around the first annular member 20.

Figure 7:
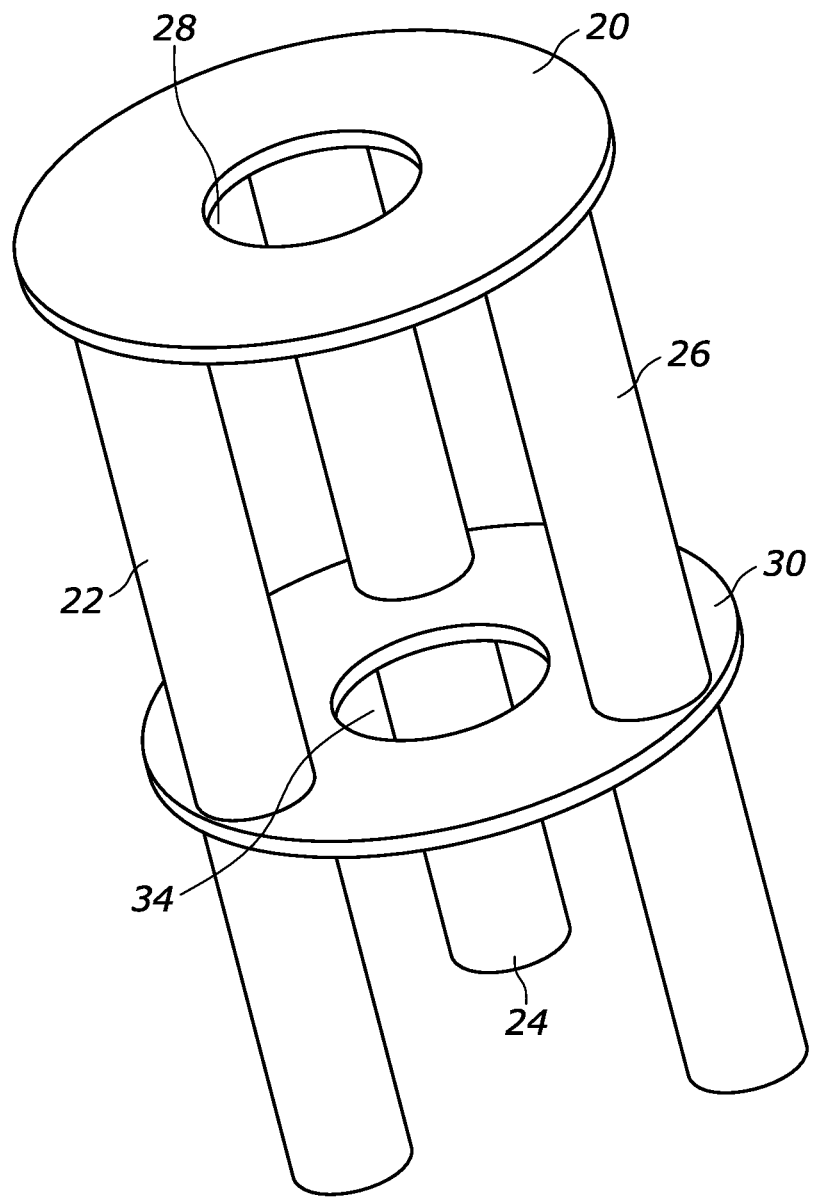
FIG. 7 is a perspective view of another example of the DMEK holder.

FIG. 7 is a perspective view of another example of a DMEK holder. As shown in FIG. 7, the DMEK holder has both a first annular member 20 with an opening 28 and a second annular member 30 with an opening 34. Both the first annular member 20 and the second annular member 30 may be ring shaped. The opening 28 in the first annular member 20 may be aligned with the opening 34 in the second annular member 30 such that a preloaded corneal tissue inserter may be inserted into the openings 28, 34 to provide support for the preloaded corneal tissue inserter during transport and handling. One or more support member 22, 24, 26 may extend downwardly from and be operatively connected to the first annular member 20 and the second annular member 30.

Figure 8:
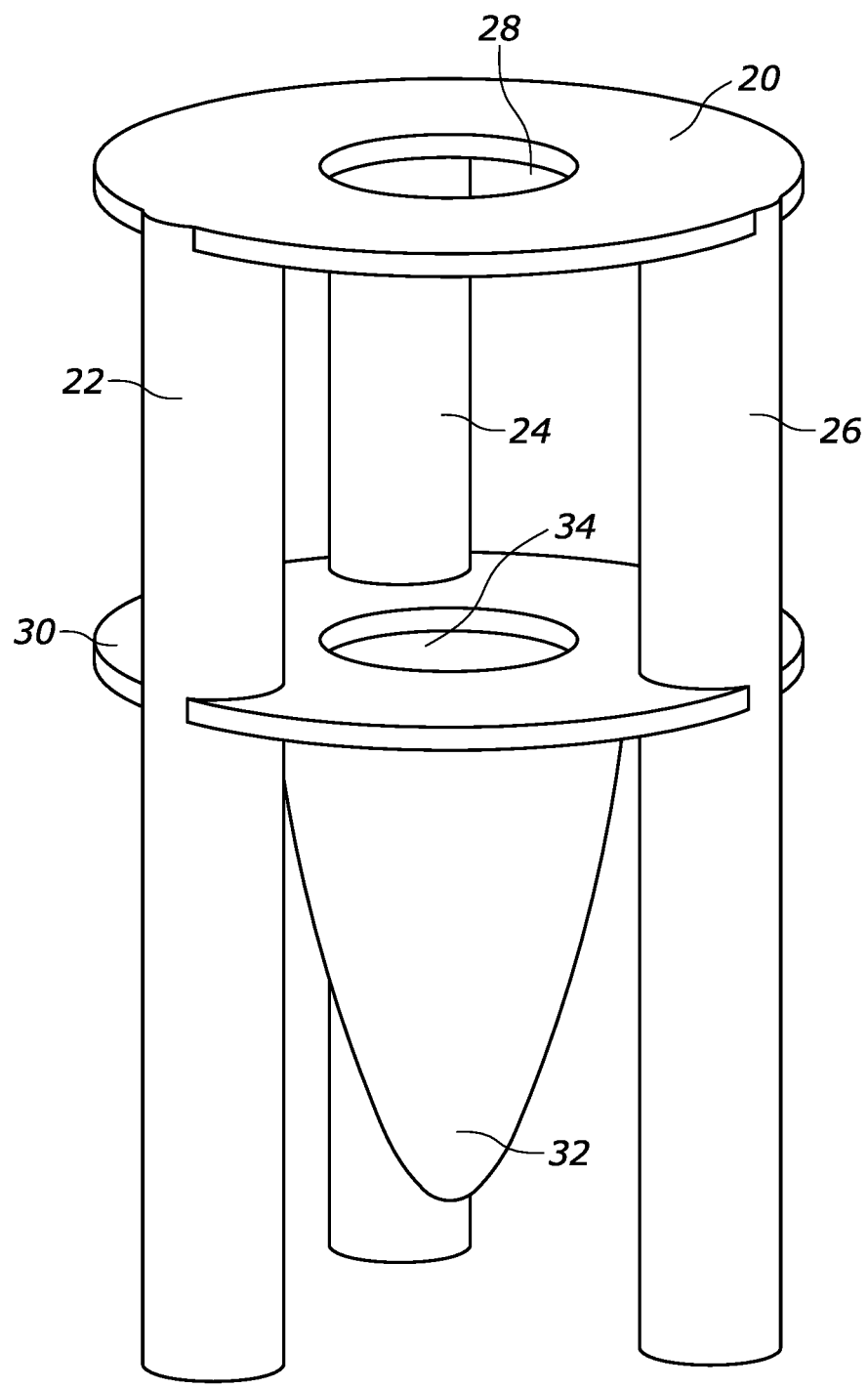
FIG. 8 is a perspective view of another example of the DMEK holder.

FIG. 8 is a perspective view of another example of a DMEK holder. As shown in FIG. 8, the DMEK holder has both a first annular member 20 with an opening 28 and a second annular member 30 with an opening 34. There is an end support 32 which may support an end of the corneal tissue inserter. The end support 32 as shown is generally conical in shape but may be otherwise shaped to support the end of the corneal tissue inserter. The end support 32 is surrounded by the support members 22, 24, 26. Note that the corneal tissue inserter when supported by the DMEK holder shown in FIG. 7 would not be in contact with the inner bottom surface of a vial. Instead the bottom or tip of the corneal inserter would be positioned within the end support 32.

Although different embodiments are shown herein for a DMEK holder it should be understood that embodiments shown include common structural elements. Therefore, it is to be understood that numerous variations are contemplated in addition to those shown. This may include variations in the number of support members or the structure of the support member(s), variations in the number of annular members or the specific size or shape of the annular members, or position(s) of the annular members along the support members, variations in whether an end support is present or not and if present, variations in the size, shape, and structure.

Thus, the present invention is not to be limited to the particular embodiments described herein. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

What is claimed is:

1. A system comprising a vial and a descemet membrane endothelial keratoplasty (DMEK) holder positioned within the vial for supporting a corneal tissue inserter, the corneal tissue inserter having a proximal end and a distal end, the DMEK holder comprising:

a top and an opposite bottom, the opposite bottom configured for placement at a bottom inner surface of the vial such that the DMEK holder extends upwardly from the bottom inner surface of the vial and towards a top end of the vial with an opening therein;

at least one support member extending vertically between the top and the bottom of the DMEK holder, with a bottom portion of the at least one support member sized and shaped to fit against the bottom inner surface of the vial to thereby support the corneal tissue inserter within the vial;

a first annular member operatively connected to the at least one support member, the first annular member having an opening sized and shaped such that the distal end of the corneal tissue inserter is insertable through the opening and the first annular member separates the corneal tissue inserter from an inner wall of the vial and positions the corneal tissue inserter within the vial away from the inner wall of the vial to thereby promote improved access to the corneal tissue inserter when the top end of the vial is open;

wherein the DMEK holder is configured to maintain the corneal tissue inserter aligned along an axis extending upwardly from the bottom inner surface, through the first annular member, and to a top end of the vial;

wherein the proximal end of the corneal tissue inserter is positioned proximate the top end of the vial to facilitate retrieval of the corneal tissue inserter and the distal end of the corneal tissue inserter extends towards the bottom inner surface of the vial.

2. The system of claim 1 wherein the at least one support member includes a first elongated support member, a second elongated support member, and a third elongated support member.

3. The system of claim 2 wherein each of the first elongated support member, the second elongated support member, and the third elongated support member is cylindrical in shape.

4. The system of claim 3 wherein each of the first elongated support member, the second elongated support member, and the third elongated support member are spaced apart around an outer edge of the first annular member.

5. The system of claim 1 further comprising a second annular member, the second annular member positioned along the at least one support member below the first annular member, the second annular member having an opening sized and shaped such that the bottom end of the corneal tissue inserter is insertable through the opening.

6. The system of claim 5 wherein the opening of the first annular member is in alignment of the opening of the second annular member.

7. The system of claim 6 further comprising an end support extending downwardly from a bottom surface of the second annular member and sized and shaped to support an end of the corneal tissue inserter.

8. The system of claim 7 wherein the end support is generally conical in shape.

9. The system of claim 8 wherein the first annular member comprises a first ring and wherein the second annular member comprises a second ring.

10. The system of claim 1 wherein the DMEK holder is integrally from plastic.

11. The system of claim 1 wherein the first annular member comprises a ring.

12. A system comprising:

a vial having a bottom end and an opposite top end, the top end having an opening for accessing contents of the vial;

a corneal tissue inserter;

a holder disposed within the vial, wherein the holder is configured to support the corneal tissue inserter in a vertically upright position along a vertical axis;

wherein the holder comprises a top and a bottom with at least one support member extending between the top and the bottom, and a first annular member at the top of the at least one support member, the first annular member having an opening therein sized and shaped such that the bottom end of the corneal tissue inserter is insertable through the opening;

wherein the holder is positioned along the vertical axis, the vertical axis extending upwardly from the bottom end of the vial, through the opening of the first annular member and to the opening at the top end of the vial.

13. The system of claim 12 wherein the corneal tissue inserter is configured for preloading with corneal tissue.

14. The system of claim 12 wherein the at least one support member includes a first elongated support member, a second elongated support member, and a third elongated support member.

15. The system of claim 14 wherein each of the first elongated support member, the second elongated support member, and the third elongated support member is cylindrical in shape.

16. The system of claim 15 wherein each of the first elongated support member, the second elongated support member, and the third elongated support member are spaced apart around an outer edge of the first annular member.

17. The system of claim 16 further comprising a second annular member, the second annular member positioned along the at least one support member below the first annular member, the second annular member having an opening sized and shaped such that the bottom end of the corneal tissue inserter is insertable through the opening.

18. The system of claim 17 wherein the opening of the first annular member is in alignment of the opening of the second annular member.

19. The system of claim 18 further comprising an end support extending downwardly from a bottom surface of the second annular member and sized and shaped to support an end of the corneal tissue inserter.

20. The system of claim 19 wherein the end support is generally conical in shape.

\* \* \* \* \*